(12) United States Patent
Kath

(10) Patent No.: US 6,461,345 B1
(45) Date of Patent: Oct. 8, 2002

(54) CANNULA OPERATED PINCH VALVE

(75) Inventor: Gary S. Kath, Scotch Plains, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/436,416

(22) Filed: Nov. 9, 1999

Related U.S. Application Data

(60) Provisional application No. 60/108,577, filed on Nov. 16, 1998.

(51) Int. Cl.⁷ .............................................. A61B 19/00
(52) U.S. Cl. ............................ 604/403; 251/4; 215/247
(58) Field of Search ........................... 604/256, 167.02, 604/167.03, 403; 137/800; 251/339, 336, 4–10, 349, 350, 355; 215/247–249

(56) References Cited

U.S. PATENT DOCUMENTS

| | | | | |
|---|---|---|---|---|
| 4,044,989 A | | 8/1977 | Basel et al. | |
| 4,447,237 A | * | 5/1984 | Frisch et al. | |
| 4,917,668 A | | 4/1990 | Haindl | |
| 4,944,736 A | | 7/1990 | Holtz | |
| 5,207,409 A | | 5/1993 | Riikonen | |
| 5,342,316 A | | 8/1994 | Wallace | |
| 5,498,253 A | | 3/1996 | Aswad et al. | |
| 5,971,181 A | * | 10/1999 | Niedospial, Jr. et al. | |
| 5,992,818 A | * | 11/1999 | Jones et al. | |
| 6,024,235 A | * | 2/2000 | Schwab | |

* cited by examiner

Primary Examiner—Mark Bockelman
(74) Attorney, Agent, or Firm—James M. Hunter, Jr.; Mark R. Daniel

(57) ABSTRACT

There is disclosed a pinch valve for allowing access to a sterile reaction vessel using a cannula. The valve remains closed until a cannula is inserted. Upon removal of the cannula, the valve automatically closes maintaining the sterile or otherwise controlled conditions of the reaction vessel.

12 Claims, 5 Drawing Sheets

CANNULA OPERATED PINCH VALVE

This Application claims the benefit of No. 60/108,577 filed Nov. 16, 1998.

BACKGROUND OF THE INVENTION

This invention pertains to a pinch valve that is accessible by means of a tapered cannula and is particularly suited for use in the fields of combinatorial and biological chemistry. The pinch valve maintains the controlled interior atmosphere of a vessel sealed with the pinch valve, yet still allows for addition or removal of material from the vessel.

It is often desirable to run chemical reactions at higher temperatures. Higher temperatures can increase the reaction rate of experiments performed under these conditions. However, experiments that involve higher temperatures and/or require the presence of volatile solvents present a number of difficulties which are not a concern when reactions are carried out at ambient temperature or with non-volatile solvents. In these high temperature experiments, if a component of the reaction mixture is to be added after the start of the reaction, or if an aliquot is to be removed before the reaction is complete, the vessel must be accessed, typically by a cannula. In accessing the vessel, quantities of the volatilized solvent may be lost to the ambient atmosphere and the sterility of the vessel may be compromised. The present invention solves this problem.

Currently, there is no commercially available valve to address this problem. Several valves have been developed to solve similar problems in surgical procedures, however, none of these are adaptable to the immediate problem. U.S. Pat. No. 4,917,668, e.g., discloses a valve for permanent venous cannulae. The '668 valve is designed to be placed directly in the bloodstream, however, its plastic construction is not rigid and durable enough for chemical applications; nor is the seal likely to be tight enough to prevent the loss of volatilized material. Many experimentally useful solvents are corrosive to plastic and therefore, these materials cannot be used in the construction of such a valve. Other devices known in the art include those disclosed in U.S. Pat. No. 5,207,409 for use as an inline member of a tubing system; in U.S. Pat. No. 5,342,316 as a placement designed to permit cannula access although exclusively through a Luer syringe cone; or in U.S. Pat. No. 5,498,253 where a device designed to permit attachment of modified tubing to packaged medical solutions is disclosed. Other pinch valves, such as those disclosed in U.S. Pat. No. 4,044,989, have been developed which utilize a piston to compress the tubing and thereby prevent access to the interior of the vessel. The pistons pinch the tubing and are controlled either manually or electrically. These valves do not reseal automatically requiring either an operator-controlled electrical signal or manual operation of an attached handle. A final approach to solve this problem is disclosed in U.S. Pat. No. 4,944,736 where an adaptor that has an attached cap which maintains the sterility of the contents of the vessel, but is not polytetrafluoroethylene (PTFE)-coated is used. This device requires removal and replacement of the cap to gain access to the material in the sealed vessel, and is designed to fit over a septum-sealed vessel. None of these devices meet all of the requirements that the valve be hemically resistant, continually accessible by cannula, reusable or disposable at the operator's discretion, and adaptable to a range of laboratory research applications.

Accordingly, there is a need in the industry for a valve that will meet all the above criteria. Methods other than pinch valves have been considered in addressing this problem, but without success. For example, septa of different compositions have been used to close and seal containers and vessels. Septum-based solutions suffer from the problem that the vessel's seal is no longer intact following the initial cannula puncture. In the case of PTFE-coated elastomeric closures, punctures leave a jagged aperture that does not reseal effectively. As a result, volatiles may escape and high temperature experiments are not feasible. Rubber septa reseal more tightly but are susceptible to corrosive solvents and can release particulate matter into the reaction mixture upon being pierced, thereby contaminating it. In both cases, large diameter cannulae make the breach more pronounced. In the case of 96 well plates, a common platform for chemical and biological reactions, a proposed solution is to cover the plate with a sheet of PTFE-coated elastomer, however this solution also fails to solve the above problems.

Thus, the primary object of the instant invention is the sealing of a vessel using a means that permits access of a tapered cannula while still maintaining the controlled atmosphere of the vessel. A further objective of the invention is the application of the invention to a chemical, biological or clinical setting. A still further object is to allow for adaptation of the invention to robotic or automated systems.

SUMMARY OF THE INVENTION

There is disclosed a device for sealing vessels which still permits access by a tapered cannula. In particular, a device comprising a metal spring or other elastomeric material surrounding a length of polytetrafluoroethylene (PTFE) tubing, which is itself encased in PTFE shrink-sleeve or other structural support is provided.

BRIEF DESCRIPTION OF THE DRAWINGS

The instant invention will be more fully understood in the following detailed description, it being understood, however, that the invention is not confined to the precise disclosure. Changes and modification may be made that do not affect the spirit of the invention, nor exceed the scope thereof, as expressed in the appended claims. Accordingly, the instant invention will now be described with particular reference to the accompanying drawings.

DETAILED DESCRIPTION OF THE INVENTION

There is disclosed a cannula operated pinch valve comprising:

a) a section of PTFE tubing which has been compressed along the middle region of the tubing;
b) a metal spring or other section of elastomeric material through which said PTFE tubing has been seated and which serves to keep said tubing in a compressed and sealed form;
c) a means of maintaining the structural integrity of the valve assembly including a screw cap; and
d) a PTFE shrink-sleeve of suitable dimensions so as to fully enclose said elastomeric material and polytetrafluoroethylene coated tubing unit upon shrinking.

Figure 1A:
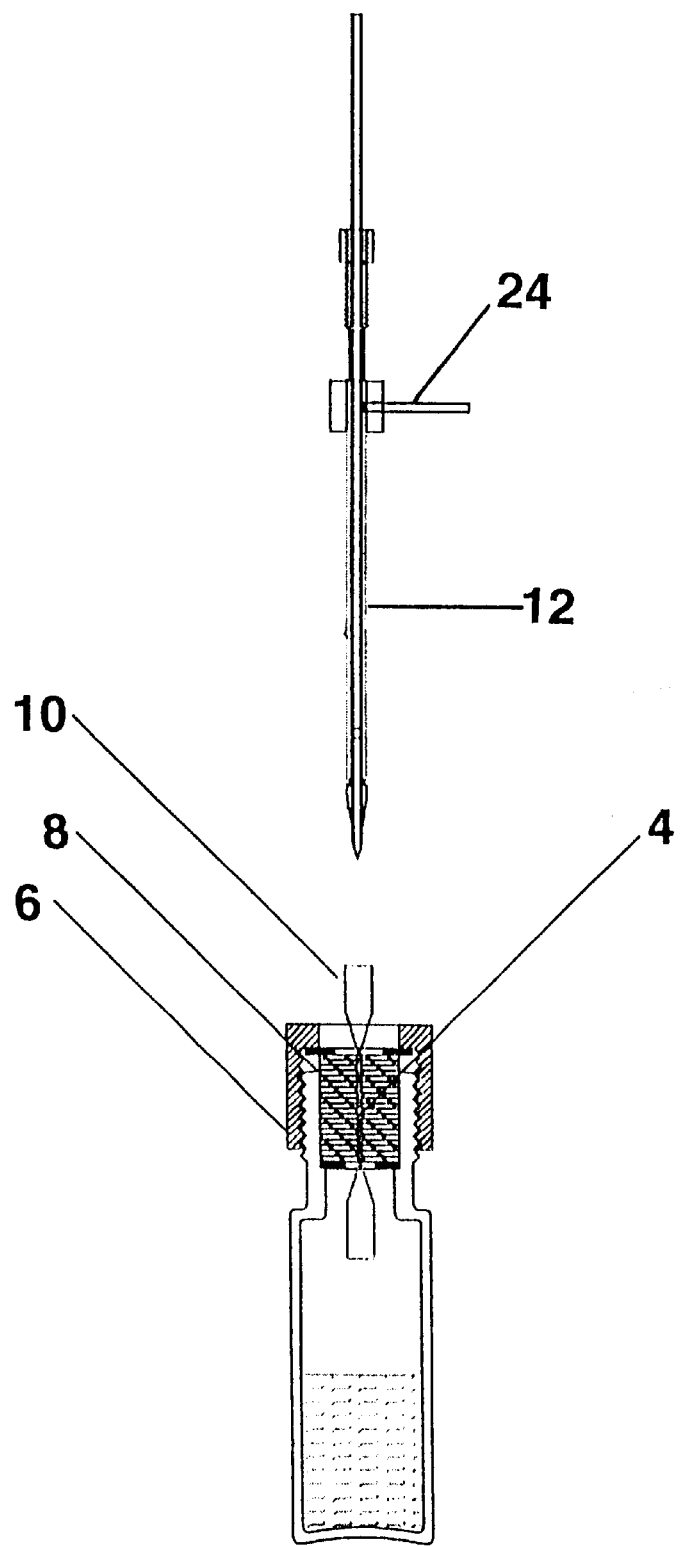
FIG. 1A shows a cross-section of one embodiment of the pinch valve assembly seated in its operational position on a reaction vessel prior to insertion of a cannula.
Figure 1B:
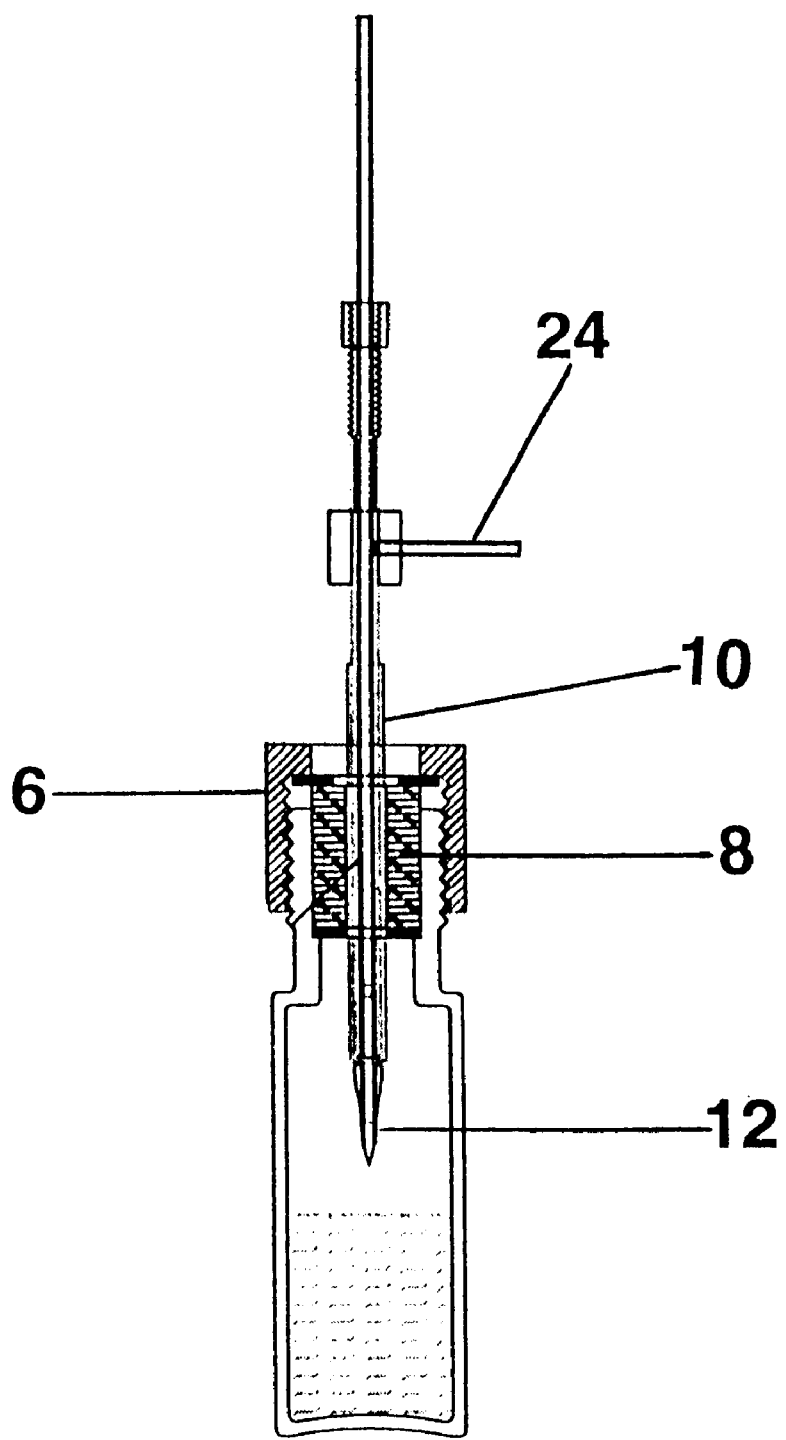
FIG. 1B shows a cross-section of one embodiment of the pinch valve assembly seated in its operational position on a reaction vessel with the cannula inserted through the pinch valve assembly.

Reference is made to the drawings wherein like numerals designate corresponding or similar elements throughout the several views. FIGS. 1A and 1B show one embodiment of the pinch valve assembly in place atop a standard vial. The assembly has three individual components: a length of PTFE tubing 10, which has been compressed in the middle region 4, by sealing means such as the silicone valve 8 shown, and a screw cap 6 which assists in maintaining the structural integrity of the valve assembly. Also shown is a tapered cannula 12 which is used to add or remove material. The cannula 12 is shown both before insertion (FIG. 1A) and in position to either add or remove material (FIG. 1B). Also shown is attachment method 24 for connection to a robotic or other type of automated system for use in high throughput screening or synthesis.

Figure 2:
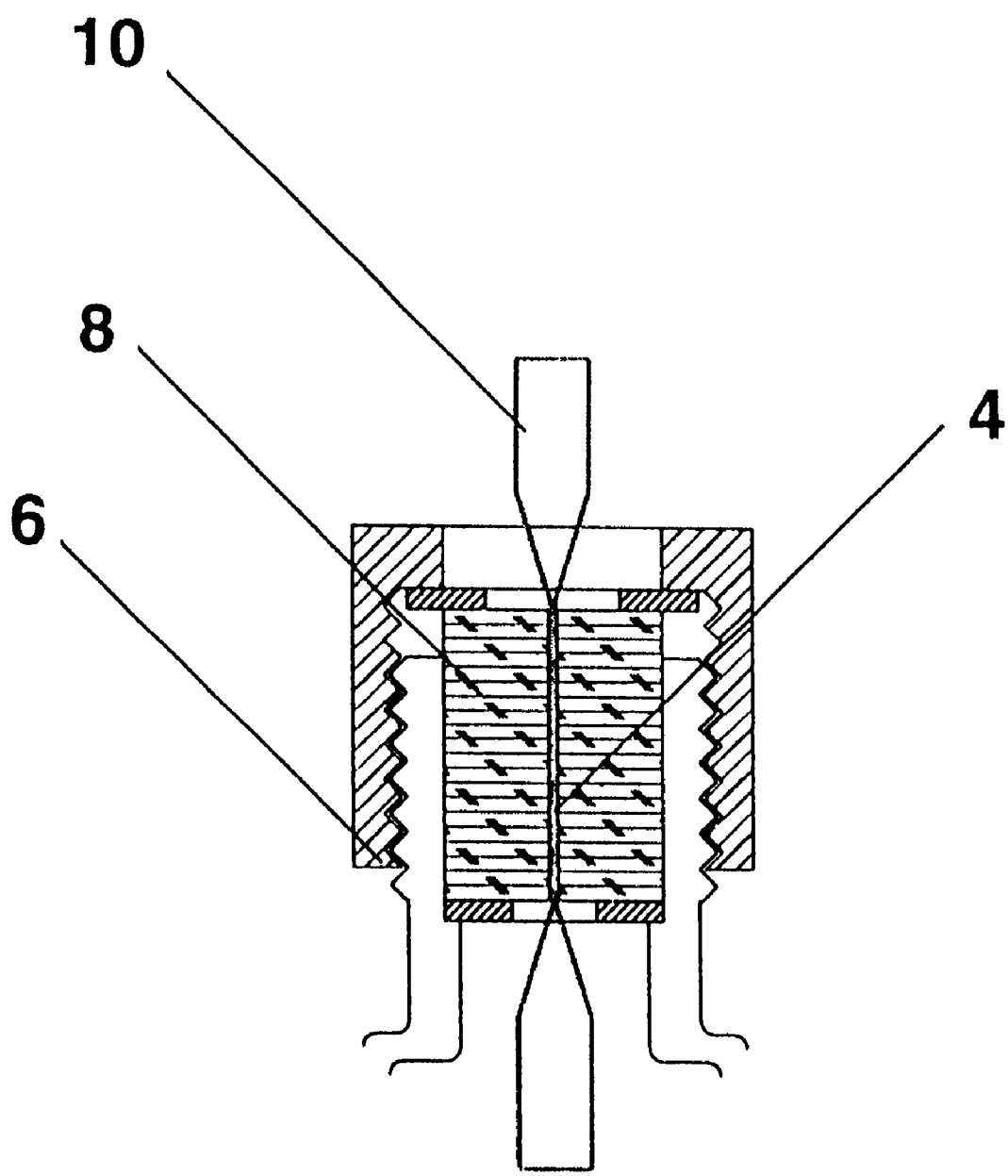
FIG. 2 shows an expanded cross-section of one embodiment of the pinch valve seated in its operational position on a reaction vessel.

FIG. 2 shows a detailed closeup view of the pinch valve assembly in place on top of a reaction vessel, in this case the standard vial depicted in FIGS. 1A and 1B. It shows the PTFE tubing 10 which has been flattened in the region of the valve-sealing material, a silicone cone 8 in this embodiment. A screw cap 6 is used to secure the pinch valve in the vial and is shown in this figure.

Figure 3A:
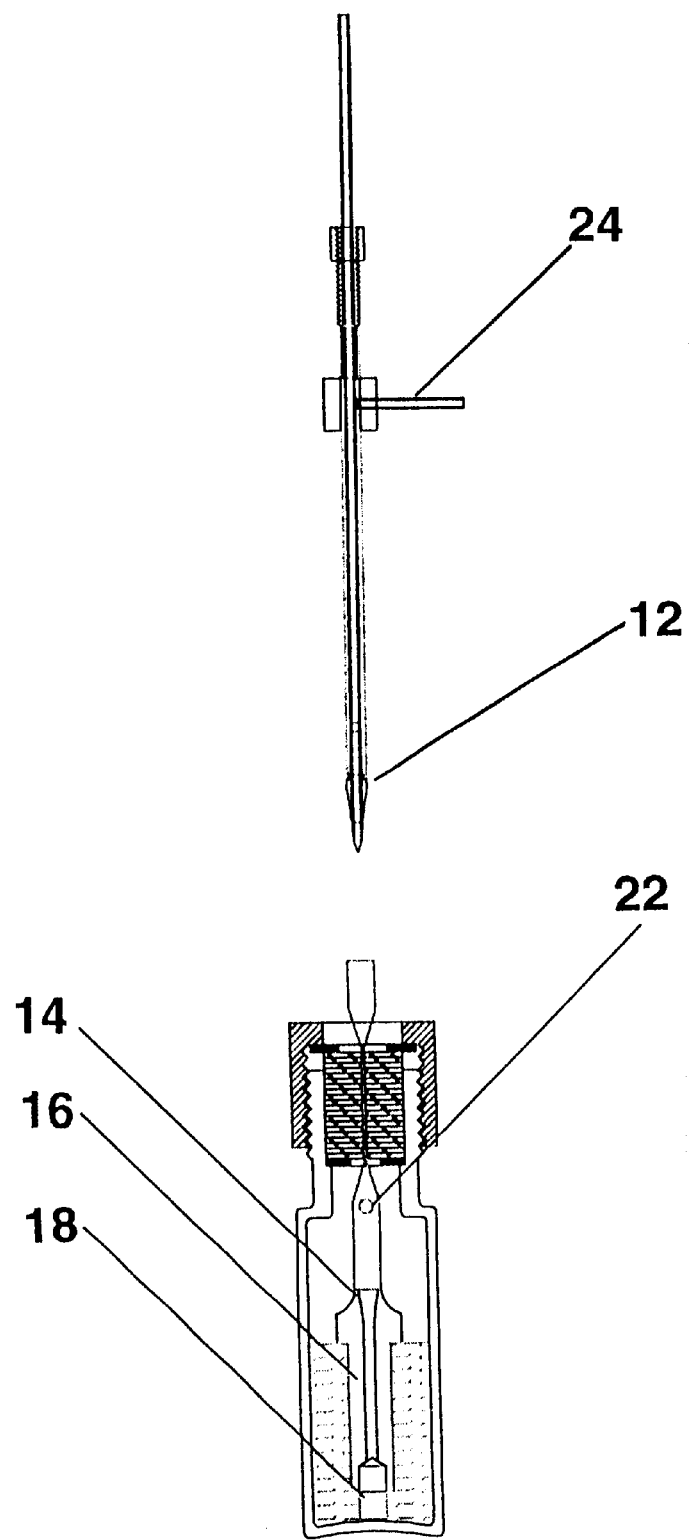
FIG. 3A shows a cross-section of one embodiment of the pinch valve fitted with a fritted sipper tube seated in its operational position on a reaction vessel prior to insertion of a cannula.
Figure 3B:
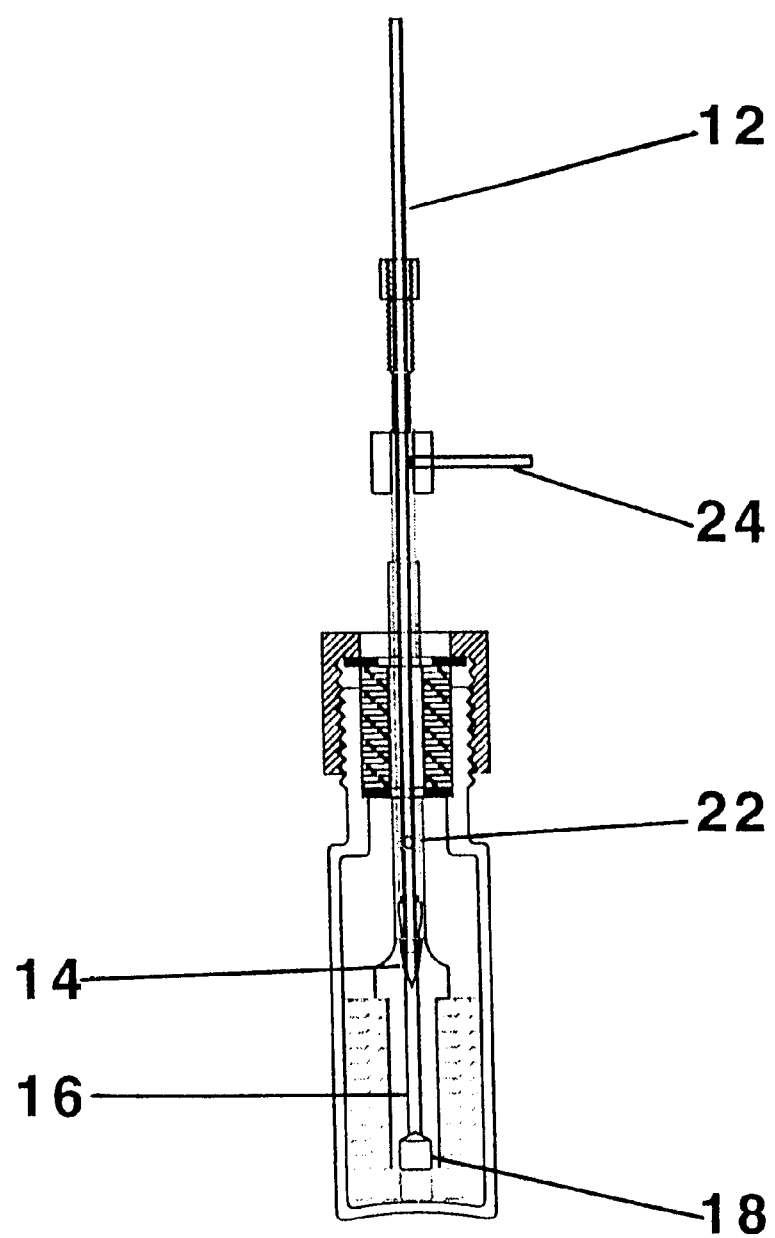
FIG. 3B shows a cross-section of one embodiment of the pinch valve fitted with a fritted sipper tube seated in its operational position on a reaction vessel with the cannula inserted through the pinch valve assembly.

FIGS. 3A and 3B show another embodiment of the pinch valve. The PTFE tubing that extends below the lowest dimension of the pinch valve is fitted with a tapered seat 14. A PTFE sipper tube 16 is attached to the tapered seat 14. The bottom end of the sipper tube is fitted with a porous frit 18 of sintered glass or other chemically-resistant material. A vent hole 22 is located on the length of the PTFE tubing just below the pinch valve assembly. FIG. 3A shows a cannula before insertion into the pinch valve assembly and FIG. 3B shows the cannula in position to either add or remove material.

In this application, the term PTFE is generally acknowledged to mean a product coated with or manufactured of a material such as TEFLON® or other suitable materials.

In operation, the pinch valve unit is seated in or over the opening of the vessel to be sealed. The insertion is made under sterile conditions, if necessary. The insertion of the pinch valve into the opening applies pressure to the material surrounding the PTFE tubing to ensure that the valve is tightly closed. When there is a need to access the material inside the vessel, a tapered cannula is used. The cannula is inserted into the top opening of the PTFE tubing, forced through the valve material and into the interior of the vessel. At this point, material may be added to or removed from the contents of the vessel. Upon completion of the required operation, the cannula is withdrawn, at which time, the valve automatically seals because of the squeezing action of the silicone cone or spring, thereby maintaining the controlled atmosphere inside the vessel.

The principles, preferred embodiments and modes of operation of the present invention have been described in the foregoing specification. However, the invention which is intended to be protected is not to be construed as limited to the particular embodiments disclosed. The embodiments are to be construed as illustrative rather than restrictive. It is recognized, however, that departures may be made therefrom within the scope of the invention, and that obvious modifications may occur to a person skilled in the art, and that the metes and bounds of the invention are to determined solely from the appended claims.

What is claimed is:

1. A cannula operated, pinch valve, for use with a reaction vessel, the pinch valve comprising:
   a) a section of PTFE tubing being compressed along a middle region thereof;
   b) a valve-sealing, elastomeric material through which the PTFE tubing is fitted, the middle region of the tubing being compressed and sealed, wherein the elastomeric material keeps the tubing compressed and sealed;
   c) a shrink-sleeve of suitable dimension fully enclosing the elastomeric material and tubing to form the pinch valve; and
   d) a cap fitted over the pinch valve to seal the pinch valve to the reaction vessel,
wherein the reaction vessel is sealed, the seal being broken by insertion of the cannula through the tubing into the reaction vessel, and the reaction vessel being re-sealed upon removal of the cannula therefrom.

2. The cannula operated, pinch valve according to claim 1, wherein the valve-sealing, elastomeric material is silicon.

3. The cannula operated, pinch valve according to claim 2, wherein the cannula is tapered for insertion into the tubing.

4. The cannula operated, pinch valve according to claim 3, wherein the reaction vessel is a vial.

5. The cannula operated, pinch valve according to claim 4, wherein the structural integrity of the pinch valve is maintained by the shrink-sleeve.

6. A cannula operated, pinch valve for fitting into a reaction vessel, the pinch valve comprising:
   a) a length of PTFE tubing being compressed along a middle region thereof, a lower region of the tubing that extends below the middle region being fitted with a tapered seat;
   b) a valve-sealing, elastomeric material through which the PTFE tubing is fitted, the middle region of the tubing being compressed and sealed, wherein the elastomeric material keeps the tubing compressed and sealed;
   c) a shrink-sleeve of suitable dimension fully enclosing the elastomeric material and tubing to form the pinch valve;
   d) a vent hole located in the lower region of the tubing;
   e) a sipper tube attached to the tapered seat of the tubing; and
   f) a cap fitted over the pinch valve to seal the pinch valve and sipper tube into the reaction vessel,
wherein the reaction vessel is sealed, the seal being broken by insertion of the cannula through the tubing into the reaction vessel, and the reaction vessel being re-sealed upon removal of the cannula therefrom.

7. The cannula operated, pinch valve according to claim 6, wherein the valve-sealing, elastomeric material is silicon.

8. The cannula operated, pinch valve according to claim 7, wherein the reaction vessel is a vial.

9. The cannula operated, pinch valve according to claim 8, wherein the structural integrity of the pinch valve is maintained by the shrink-sleeve.

10. The cannula operated, pinch valve according to claim 9, wherein the reaction vessel is a vial.

11. The cannula operated, pinch valve according to claim 10, wherein the sipper tube is fitted with a porous frit of sintered glass.

12. A method of adding material to and removing material from a sealed reaction vessel, the reaction vessel being fitted with a cannula operated, pinch valve characterized as a length of PTFE tubing being compressed along a middle region thereof; a valve-sealing, elastomeric material through which the PTFE tubing is fitted, the middle region of the tubing being compressed and sealed; a shrink-sleeve of suitable dimension fully enclosing the elastomeric material and tubing to form the pinch valve; and a cap fitted over the pinch valve to seal the pinch valve into the reaction vessel, the method of adding and removing material, comprising the steps of:

a) inserting a tapered cannula into the PTFE tubing through the compressed, middle region of the tubing into the reaction vessel, wherein the seal of the pinch valve is broken;

b) adding material to or removing material from the reaction vessel by way of the cannula; and c) withdrawing the cannula from the PTFE tubing through the compressed, middle region of the tubing to re-seal of tubing, wherein material cannot be added to or removed from the reaction vessel.

* * * * *